United States Patent
Muraki et al.

(10) Patent No.: US 6,766,047 B2
(45) Date of Patent: Jul. 20, 2004

(54) DEFECT INSPECTION METHOD FOR THREE-DIMENSIONAL OBJECT

(75) Inventors: Yutaka Muraki, Yokohama (JP); Taro Akabane, Yokohama (JP); Masami Takeshi, Yokohama (JP); Naoya Murota, Hamamatsu (JP)

(73) Assignee: Suzuki Motor Corporation, Shizuoka-Ken (JP)

( * ) Notice: Subject to any disclaimer, the term of this patent is extended or adjusted under 35 U.S.C. 154(b) by 210 days.

(21) Appl. No.: 10/005,637

(22) Filed: Dec. 5, 2001

(65) Prior Publication Data

US 2002/0070363 A1 Jun. 13, 2002

(30) Foreign Application Priority Data

Dec. 12, 2000 (JP) ............................. 2000-377116

(51) Int. Cl.[7] .................................................. G06K 9/18
(52) U.S. Cl. .................................................... 382/149
(58) Field of Search ..................... 382/149; 356/237.3, 356/394, 237; 438/16, 7

(56) References Cited

U.S. PATENT DOCUMENTS 5,430,548 A * 7/1995 Hiroi et al. ................. 356/394
5,680,207 A * 10/1997 Hagiwara ................. 356/237.3
6,487,307 B1 * 11/2002 Hennessey et al. ......... 382/149

FOREIGN PATENT DOCUMENTS

| JP | 1010053 | 1/1998 |
|---|---|---|
| JP | 10-010053 | 1/1998 |

* cited by examiner

Primary Examiner—John F. Niebling
Assistant Examiner—Andre' C. Stevenson
(74) Attorney, Agent, or Firm—Darby & Darby

(57) ABSTRACT

A defect inspection method for three-dimensional shapes employs a difference is between a distance code obtained by scanning, a perfect work (a value indicating a rocking angle of a mirror), and a distance code obtained by scanning an inspected work, at each measurement position. Differences are stored for a matrix in which a linear direction of the irradiation and a direction of a moving locus of the irradiation are two orthogonal axes. The most frequent difference value among matrix elements in the linear direction of the irradiation is found at each rocking angle of the mirror. A matrix element having a difference that deviates from the most frequent difference value by more than a set value is found at each rocking position of the mirror. Thus, sections having distance codes that do not match distance codes of the perfect work even by relatively shifting the distance code data are detected and identified as defect candidates. The presence/absence of defects on the inspected work is determined on the basis of all the existing states of matrix elements as defect candidates.

6 Claims, 9 Drawing Sheets

DEFECT INSPECTION METHOD FOR THREE-DIMENSIONAL OBJECT

BACKGROUND OF THE INVENTION

1. Field of the Invention

The present invention relates to an improved defects inspection method of a three-dimensional shape.

2. Description of the Related Art

As a method of detecting surface defects of a three-dimensional work for instance, Japanese Unexamined Patent Application Publication No. 10-10053 discloses a method of detecting a defect based on a change or a differential at the boundaries of patterns by irradiating striped-pattern beams on the work.

However, this method detects the presence or absence of defects based simply on changes in the brightness on the work. Thus, it is difficult for the method to detect defects on the surface of work that can form shadows due to complex projections or recessed shapes or that have different shades due to oil contamination or marking made by a marker. This method often produces false alarms by detecting normal marks caused by oil contamination or markings made by a marker as defects.

In order to solve such a problem, defect inspection methods have been invented which use the three-dimensional shape of an object being inspected in accordance with know trigonometric measurement principles.

The principle of a defect inspection method using a three-dimensional shape based on trigonometric measurement principle is explained briefly with reference to FIG.6 (a).

A light projector 1, for example, a laser beam, emits a beam which is directed by a mirror 3 to linearly irradiate a work 2 with a pattern having a width in the thickness direction (X-axis direction) of FIG. 6(a). A mirror driving means (not shown in the figure) rocks the mirror 3 at a predetermined pitch in a direction which moves the locus of radiation orthogonal to the linear irradiation, in other words, in a direction which moves the radiation in the right-to-left direction (Y-axis direction) of FIG. 6(a). A rotating position detecting means (not shown in the figure) detects the rocking position of the mirror 3. A camera 4 takes a picture of the work 2 at each rocking position of the mirror 3 by maintaining a predetermined relative position with respect to the mirror 3. An image processing unit 5 finds the projection/recess shapes of the work 2 by storing a value (mentioned as a distance code hereinafter) indicating the rocking angle of the mirror 3 for a matrix of laser beam detecting positions in a camera coordinate system of the camera 4 for which the linear direction of the irradiation and the moving locus of radiation are two orthogonal axes.

A line L1($\alpha$) shown in FIG. 6(a) is the optical path of the laser beam that is reflected by the mirror 3 to irradiate the work 2. A line L2 is a straight line connecting the point on the work 2 irradiated by the laser beam to the camera 4.

The position of the mirror 3 relative to the camera 4, in other words, the length of the straight line connecting the mirror 3 and the camera 4, remains constant. An angle between the straight line connecting the mirror 3 and the camera 4 and the line L1 is easily found given knowledge of the rocking angle of the mirror 3.

An angle between the straight line connecting the mirror 3 and the camera 4, and the line L2 is calculated as an angle between the line L2 and the optical axis of the camera 4 on the basis of the detected laser beam position on a camera coordinate system of the camera 4.

Accordingly, although it is possible to find distance between the camera 4 and the work 2 in accordance with the trigonometrical measurement principle, the computation is complex and requires a long time for computation. Thus, instead of calculating the distance between the camera 4 and the work 2, the rocking angles of the mirror 3 which are related to the distances, are stored as a corresponding matrix of a laser beam detecting position on a camera coordinate system of the camera 4. Therefore, the shape of the work 2 is stored and the need for a complex computation is omitted.

For instance, if it is assumed that a matrix (X, Y) on a camera coordinate system for which the linear direction of the irradiation and the moving locus direction of the irradiation are two orthogonal axes consists of n-row by m-column matrix elements $(i_1, j_1)$ to $(i_n, j_m)$. Then, if the rocking angle of the mirror 3 is $\alpha$ when the irradiated beam is detected at $(X_{(x=1\ to\ n)}, j)$ on the camera coordinate system as shown in FIG. 6(a), the $\alpha$ value is stored in all of the n matrix elements in the X-axis direction of the matrix $(X_{(x=1\ to\ n)}, j)$ on the camera coordinate system. It is found that the height of the work 2 (shown only with a solid line) is the same at a section where radiation hits, since the $\alpha$ value is constant.

If there is a protrusion 2f (as shown with a chain line in FIG. 6(a)) at the location (i, j) on the surface of the work 2, the irradiation does not hit the top face of the protrusion 2f when the rocking angle of the mirror 3 is $\alpha$. Irradiation hits the top face of the protrusion 2f when, for example, the rocking angle of the mirror 3 is $\alpha'$. Thus, the $\alpha'$ value is stored only at the position of the protrusion 2f, which is (i, j), among the n matrix elements in the X-axis direction of the matrix $(X_{(x=1\ to\ n)}, j)$ on the camera coordinate system Accordingly, the existence of the protrusion 2f on the work 2 is confirmed based on a difference between the rocking angles $\alpha$ and $\alpha'$.

The processing unit 5 repeatedly executes the above-mentioned processing; that is the rocking angles of the mirror 3, in other words, distance code values are stored at each rocking position of the mirror 3 for a matrix of a laser beam detecting positions in the camera coordinate system of the camera 4 while the mirror 3 is rocked to shift the radiation in the Y-axis direction.

FIG. 7(a) is one example of an image when a distance code value on each matrix is shaded and visualized by making a distance code value stored at each matrix element correspond to a gray-scale density. For instance, the distance code value is 0 (black on a gray scale) when the irradiation is at the right end of the work 2, and the distance code value is 255 (white on a gray scale) when the irradiation is at the left end of the work 2. Such an image is referred to as a distance code image hereinafter.

When a surface defect of the work 2 is detected based on such a principle, the projection/recess shape of the perfect work 2 is first found by the image processing unit 5. Then, the distance code image of the perfect work 2 is obtained as shown in, for instance, FIG. 7(a). The distance code image is mentioned as a distance code image as a reference.

Subsequently, the projection/recess shape of the inspected work 2 is similarly found as described above by the image processing unit 5, thus obtaining a distance code image of the inspected work 2. FIG. 7(b) is an example of a distance code image obtained from the inspected work 2 having a defect 6 at the center.

Then, the presence/absence of a defect on the inspected work 2 is determined by a comparison at each matrix element ($i_{x\ (x=1\ to\ n)}, j_{y\ (y=1\ to\ m)}$) between distance codes stored in a reference distance code image obtained from the perfect work 2, and distance codes stored in a distance code image obtained from the inspected work 2.

Specifically, a reference distance code image as shown in FIG. 7(a) is first compared with a distance code image as an inspection object shown in FIG. 7(b) to find a difference of distance codes at each matrix element ($i_{x\ (x=1\ to\ n)}, j_{y\ (y=1\ to\ m)}$). This difference is stored for each matrix element ($i_{x\ (x=1\ to\ n)}, j_{y\ (y=1\ to\ m)}$). As the scale of a difference of distance codes is visualized as a corresponding gray-scale density, as described above, an image shown in, for example, FIG. 7(c) is obtained. Such an image is referred to as a differential distance code image hereinafter.

Furthermore, as image processing is carried out for the differential distance code image by eliminating noise or the like, the defect 6 becomes visible and the presence/absence of a defect on the inspected work 2 is easily determined. Such an image is mentioned as a defect extracting image hereinafter.

As such a method is applied, the presence/absence of a defect is determined based on an absolute difference in projection/recess shapes of the surface of the work 2. Thus, a defect is properly detected while significantly reducing negative effects due to a change in density of the image which is caused by shadows on the work 2, oil contamination, markings made by a marker, or the like.

However, in the trigonometrical measurement principle, the rocking position of the mirror 3 has to be controlled with high precision. If there is a slight error in the rocking position of the mirror 3, a serious error is found in distance codes relating to the surface shapes of the work 2.

Subsequently, the reasons why such a problem is found will be explained briefly by referring to FIGS. 8(a) to 8(e). FIG. 8(a) is an example of a shape of the work 2 where a distance code image is obtained. The work 2 has a peripheral groove 2a having a rectangular cross-section at the outer periphery and a peripheral groove 2b having a wedge-shaped cross-section. The work 2 has a flat part 2c that is curved in a recessed shape at the center thereof.

A–A' in FIG. 8(a) shows the linear direction (X-axis direction) of laser beams irradiated from the mirror 3, and B–B' indicates the direction (Y-axis direction) of a moving locus of radiation.

Only the flat Dart where the linear direction (X-axis direction) of radiation on the work 2 overlaps with the line B–B' is focused upon, and FIG. 8(b) shows the data of relations between matrices of laser beam detecting positions and distance codes at a reference temperature (for instance, 15° C.). In FIG. 8(b), while distance code 0 is a reference value at the right end of the work 2, distance code 255 is a reference value at the left end of the work 2. The data is visualized to horizontally locate these values.

The height of the work 2 is always constant in this example without depending on where beams radiate on B–B', in otherwords, which rocking position the mirror 3 has. Thus, the graph in FIG. 8(b) is flat with a constant Z value where the direction of a moving locus of radiation (Y-axis direction) is the horizontal axis and the height of the work 2 is the vertical axis (Z-axis direction).

FIG. 8(c) shows relations between matrices of laser beam detecting positions and distance codes when the same work 2 is measured at a temperature higher than the reference temperature. As clearly shown in FIG. 8(b) and FIG. 8(c), in the distance code data measured at the temperature higher than the reference temperature, the reference values of distance codes are adjusted so as to provide the same height at the right and left ends of the work 2. However, as radiation shifts toward the right side (+ direction of Y-axis) of the work 2, incorrect measurement results are obtained as if distance codes values gradually increase.

This is an abnormality of measurement due to the error of rocking positions of the mirror 3 mentioned above. For instance, it is assumed that, in FIG. 6(b), the mirror 3 moves to 3b instead of 3a as a correct rocking position, due to a positional error caused by the temperature rise. If the mirror 3 is at the correct position 3a to irradiate the laser beam along the line L1 and the camera 4 can capture the laser beam at the position ($X_{(x=1\ to\ n)}$, j) on the camera coordinate system, the rocking angle of the mirror 3, in other words, the distance code value, corresponds thereto and is stored.

However, the mirror 3 is actually displaced to 3b. Although laser beam is irradiated along the line L1' and detected at ($X_{(x=1\ to\ n)}$, j+Δj) on the camera coordinate system, the image processing unit 5 itself does not recognize it and determines that the laser beam irradiated along the line L1 is detected at ($X_{(x=1\ to\ n)}$, j+Δj) on the camera coordinate system. As a result, the image processing unit 5 stores the distance code α corresponding to a rocking angle, which should have been primarily stored at ($X_{(x=1\ to\ n)}$,j+Δj) on the camera coordinate system, at the position of ($X_{(x=1\ to\ n)}$,j+Δj) on the camera coordinate system (position where α should have been stored as a primary distance code). Accordingly, an incorrect measurement results as shown in FIG. 8(c). In other words, the a distance code which is larger than the primary α' distance code, is stored at the position to the right end on the camera coordinate system, so that a contradiction, as shown in FIG. 8(c), is found. Moreover, as clearly shown in FIG. 6(a), it is determined that the height of a surface is higher at a section with a smaller distance code (α'<α) at each matrix position on the same line with the same Y on the camera coordinate system, for example, at ($X_{(x=1\ to\ n)}$,j).

FIG. 9(a) shows an example of a distance code image formed on the basis of distance codes which are measured at a temperature higher than the reference temperature. The distance code image shown in FIG. 9(a) is compared with the distance code image prepared at the reference temperature shown in FIG. 7(a) to find differences of the distance codes. Then, a differential distance code image as shown in FIG. 9(b) is obtained. As clearly shown in FIG. 9(b), the difference values become large toward the right side (+ direction of the Y-axis) of the differential distance code image due to the above-mentioned distance code error. When a defect extracting image is formed based on the differential distance code image, an area having large differences remains at the right side (+ direction of the Y-axis) section where no defects primarily exist. This section is extracted as a defect, so that the work 2 that is primarily a good product, is determined to be an inferior product.

As a method to solve such a problem, distance code images are prepared as references at various temperatures, and the reference distance code images are chosen depending on the temperature under which an inspection is performed.

However, in order to prepare a plurality of distance code images as references, the image processing unit 5 must have a large memory. Moreover, due to temperature changes depending on time even in the same day, distance code images as references have to be repeatedly re-selected within the same day and measurement procedures become troublesome.

On the contrary, temperature could be kept constant by controlling the measurement environment. However, in this case, the equipment required for temperature control is large, which is troublesome.

OBJECTS AND SUMMARY OF THE INVENTION

Accordingly, it is an object of the present invention to solve the conventional problems mentioned above, and to provide a defect inspection method of a three-dimensional shape that can accurately inspect detects on a work surface without changing the settings in accordance with temperature changes, and without actively controlling the temperature of the environment.

The defect inspection method of a three-dimensional shape according to the present invention provides a light projector emitting a laser beam, a mirror to reflect the laser beam from the light projector to linearly irradiate a work, a mirror driving means to rock the mirror at a predetermined pitch in a direction where a moving locus of the irradiation is orthogonal to the linear irradiation, a camera to take a picture of the work at each rocking position of the mirror by maintaining a predetermined position with respect to the mirror and an image processing unit to find a projection/recess shape of the work by storing values which indicate rocking angles of the mirror for laser beam detecting positions on a camera coordinate system for which the linear direction of the irradiation and the direction of a moving locus of the irradiation are two orthogonal axes. A projection/recess shape of a perfect work is found and then stored by the image processing unit in advance. Then, a projection/recess shape of an inspected work is found by the image processing unit. The presence/absence of a detect on the inspected work is inspected by comparing, at each matrix element, a value indicating a rocking angle of the mirror stored for the perfect work to a value indicating a rocking angle of the mirror stored for the inspected work. In order to achieve the object above, in particular, a difference is found between a value indicating a rocking angle of the mirror stored for the perfect and a value indicating a rocking angle of the mirror stored for the inspected work, at each matrix element. This difference is stored for each matrix element. A most frequent difference value is found among matrix elements in a linear direction of the irradiation for each column of the matrix elements arranged in a direction of the irradiation. Matrix elements having differences deviating from the most frequent difference value by more than a set level are found at each column of the matrix elements. These elements are stored as defect candidates. Then, the presence/absence of defects on the inspected work is determined based on all the existing states of the matrix elements as defect candidates on the matrix.

Subsequently, the principles of how the invention solves the conventional problems will be explained.

First, a light projector, a mirror driving means, a camera, and an image processing unit are operated. As in the conventional art, the projection/recess shape of a perfect work is found and then stored by storing values indicating rocking angles of the mirror, in other words, distance codes, for a matrix of a camera coordinate system for which the linear direction of the irradiation and the moving locus of the irradiation are two orthogonal axes. Accordingly, a distance code image shown in, for instance, FIG. 7(a) is obtained as a reference.

Subsequently, as mentioned above, the light projector, the mirror driving means, the camera, and the image processing unit are operated repeatedly. A distance code is stored for a matrix of a camera coordinate system for which the linear direction of the irradiation and the moving locus of the irradiation are two orthogonal axes, and the projection/recess shape of the inspected work is found. Accordingly, a distance code image shown in, for example, FIG. 9(a) is obtained. Normally, environmental temperature is different from the temperature when the distance code image was obtained as a reference. Thus, the distance code image shown in FIG. 9(a) has an error in distance codes due to a positional shift of the mirror or a detection error (nonlinear shift, origin drift, or the like) of rocking positions caused by temperature drift or the like of a rotating position detecting means for detecting the rocking position of the mirror.

Subsequently, the difference between the distance codes of the perfect work and the distance codes of the inspected work at each matrix element for which the direction of the irradiation and the direction of a moving locus of the irradiation are two orthogonal axes. This difference is then stored for each matrix element. Accordingly, a differential distance code image shown in, for example, FIG. 9(b) is obtained. Since the distance code image of the inspected work has an error by itself, the difference values of distance codes increase toward the end of the work, as shown in FIG. 8(c).

However the distance code image of the inspected work has errors because of the drift of rocking angles of the mirror or the erroneous recognition of rocking angles. Thus, the distance codes stored for matrix elements in the same column in the direction of irradiation should all have equal errors. For instance, when the work 2 shown in FIG. 8(a) is inspected, the distance code data at the end of the work 2 measured at the reference temperature is shown as a broken line in FIG. 8(d) where the horizontal axis is the linear direction (X-axis direction) of irradiation. Moreover, the distance code data at the end of the work 2 measured at a temperature higher than the reference temperature is shown as a solid line in FIG. 8(d). Thus, either the distance code data of the work 2 measured at the reference temperature or the distance code data of the work 2 measured at a temperature higher than the reference temperature is shifted, and both are overlapped as shown in FIG. 8(e). Then, the presence/absence of a surface defect is found by determining the presence/absence of mismatching distance code data at each position in the column of matrix elements in the direction of irradiation (X-axis direction).

First, most frequent difference values are found at each column of matrix elements arranged in the direction of the irradiation, among matrix elements in the linear direction of the irradiation. When the inspected work 2 has no defects on its surface, both should match completely, as in FIG. 8(e), when the distance code data of the work 2 measured at the reference temperature is overlapped with the distance code data of the work 2 measured at a temperature higher than the reference temperature. In this case, all the difference values found in matrix elements in the linear direction of irradiation are equivalent to $\Delta Z$. It is obvious that differences other than $\Delta Z$ are sometimes detected when the work 2 has a projection/recess defect on its surface. However, since the surface of the work 2 is not normally severely damaged, most frequent differences in matrix elements in the linear direction of the irradiation are always equivalent to $\Delta Z$ in FIG. 8(d). This $\Delta Z$ is equivalent to a shift quantity. Furthermore, $\Delta Z$ because a distance code error itself due to a positional shift of the mirror or a detection error (nonlinear shift, origin drift, or the like) caused by temperature drift or the like of a rotating position detecting means for detecting the rocking position of the mirror.

Subsequently, matrix elements having differences which deviate from the most frequent difference value ($\Delta Z$) by more than a set value are found at each column of matrix elements arranged in the direction of the irradiation, and are stored as defect candidates. The matrix element section having differences deviating from the most frequent difference value ($\Delta Z$) by more than a set value is a section where the distance code data of the work measured at the reference temperature and the distance code data of the work measured at a temperature higher than the reference temperature do not match each other, even by shifting the distance code data. This indicates that the section has projection/recess defects.

Finally, the presence/absence of defects on an inspected work is determined in accordance with the existing state of all matrix elements which is defect candidates on a matrix. That is, all the defect candidates within a projection plane of the work for which the linear direction of irradiation and the direction of a moving locus of irradiation are found along two orthogonal axes. For instance, when a point defect candidates are found, it is considered to be simply a measurement mistake. It is also possible to determine that a work has no abnormality. When defect candidates are close to each other over a certain area, it is possible to clearly determine that they are surface defects.

Therefore, the scale ($\Delta Z$) of a distance-measuring code error caused by a position shift of the mirror or a detection error (nonlinear shift, origin drift or the like) due to temperature drift or the like of a rotating position detecting means for detecting the rocking portion of the mirror is found. Then, a test is performed to determine whether or not the distance code data of the work measured at the reference temperature match the distance code data of the work measured at a temperature higher than the reference temperature by shifting the distance code data by an amount equivalent to an error. Accordingly, appropriate defect inspection can always be performed independently of temperature differences during measurement.

The problems are solved as described above even when the measurement is performed at a temperature lower than the reference temperature.

In order to achieve the same object as above for each projection/recess shape of a perfect work and projection/recess shape of an inspected work, a value which indicates a most frequent rocking angle of a mirror is found among matrix elements in the linear direction of irradiation at each column of matrix elements arranged in the direction of irradiation. In order to match the values that indicate most frequent rocking angles of a mirror in the projection/recess shape of a perfect work and projection/recess shape or an inspected work, the values for the inspected work are shifted at each column of matrix elements arranged in the direction of irradiation. Then, the values indicating rocking angles of the mirror that are stored for the perfect work are compared, at each matrix element, with the values indicating rocking angles of the mirror that are stored for the inspected work, so as to detect the presence/absence of defects on the inspected work.

In this case, the values indicating the most frequent rocking angles of a mirror are equivalent to a straight line having the maximum length in the linear direction of irradiation on a work. (However, this is based on the assumption that the straight line is orthogonal to the optical axis of a camera.) Thus, this straight line is specified at each perfect work and an inspected work. Then, the data values indicating rocking angles of a mirror are shifted and compared at each column of matrix elements arranged in the direction of irradiation so as to overlap these straight lines. This permits proper detection of defects regardless of temperature differences during measurement. This shift quantity is equal to the scale ($\Delta Z$) of a distance code error caused by the above-mentioned position shift of the mirror or error (nonlinear shift, origin drift, or the like) due to temperature drift or the like of a rotating position detecting means for detecting the rocking position of the mirror.

The above, and other objects, features and advantages of the present invention will become apparent from the following description read in conjunction with the accompanying drawings, in which like reference numerals designate the same elements.

DETAILED DESCRIPTION OF PREFERRED EMBODIMENTS

Figure 1:
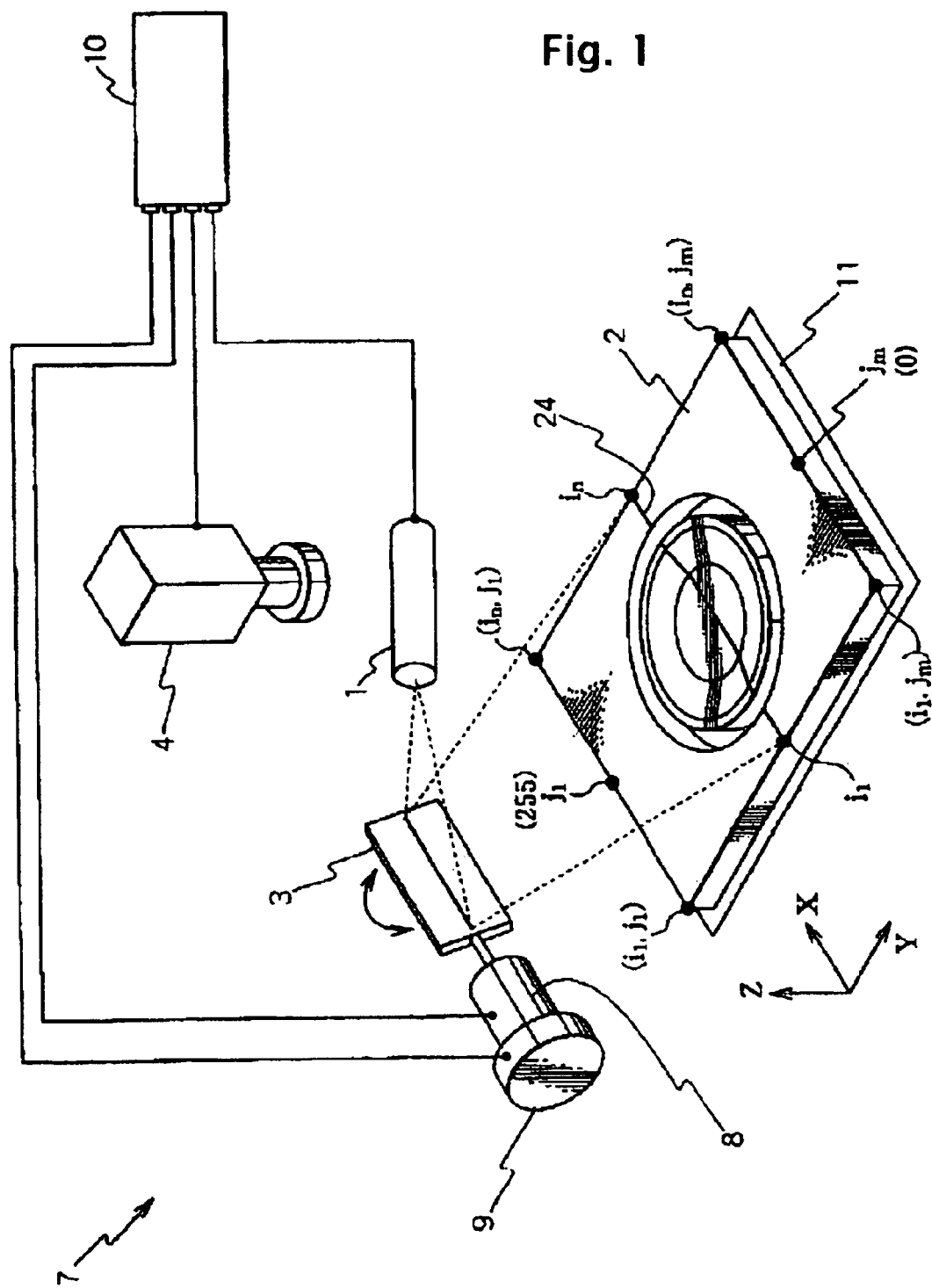
FIG. 1 is a functional block diagram showing a schematic configuration of a defect inspection device required to carry out a defect inspection method of a three-dimensional shape according to the present invention.

Referring to FIG. 1, a defect inspection device 7 has a light projector 1 irradiating a laser beam. A mirror 3 reflects the laser beam from the light projector 1 to linearly illuminate a work 2 in the direction of an X-axis in FIG. 1. A galvano scanner 8 drives the mirror 3 with a rocking motion at a predetermined pitch in the direction where the moving locus of the irradiation is orthogonal to the linear radiation. That is, the rocking motion moves the impact point of the beam in the direction of the irradiation toward a Y-axis in FIG. 1. A rotating position detecting sensor 9, attached to the galvano scanner 8, detects the rocking position of the mirror 3. A camera 4 to take a picture of the work 2 at each rocking position of the mirror 3 by maintaining a relative position with respect to the mirror 3. A work mounting table 1 recesses the work 2 on its surface.

The light projector 1, the galvano scanner 8 and an image processing unit 10 which is also a drive control means of the camera 4, detect the projection/recess shape of a surface of the work 2 by repeatedly executing a process to store values indicating the rocking angles of the mirror 3 (distance codes) in response to laser beam detecting positions on a camera coordinate system of the camera 4, while rocking the mirror 3 so as to store the distance codes in response to a matrix (X, Y) on the camera coordinate system for which the linear direction (X-axis direction) of the irradiation and the direction of a moving locus (Y-axis direction) of the irradiation are two orthogonal axes.

Figure 6:
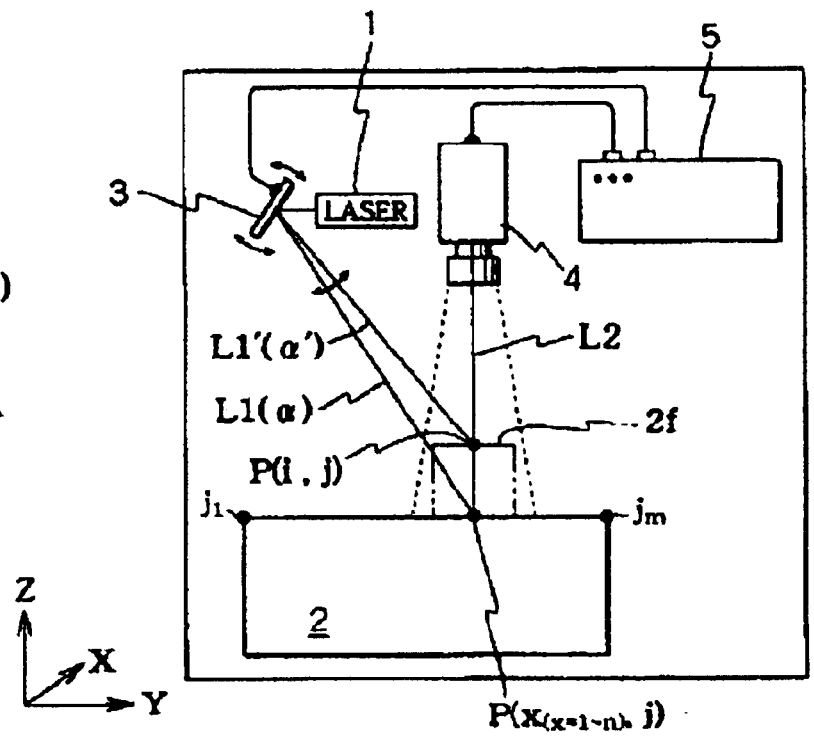
FIG. 6(a) is a conceptual diagram to which reference will be made in explaining the principle of a conventional defect inspection method of a three-dimensional shape.
FIG. 6(b) is a conceptual diagram to which reference will be made in explaining problems found in the conventional defect inspection method of a three-dimensional shape.
Figure 6:
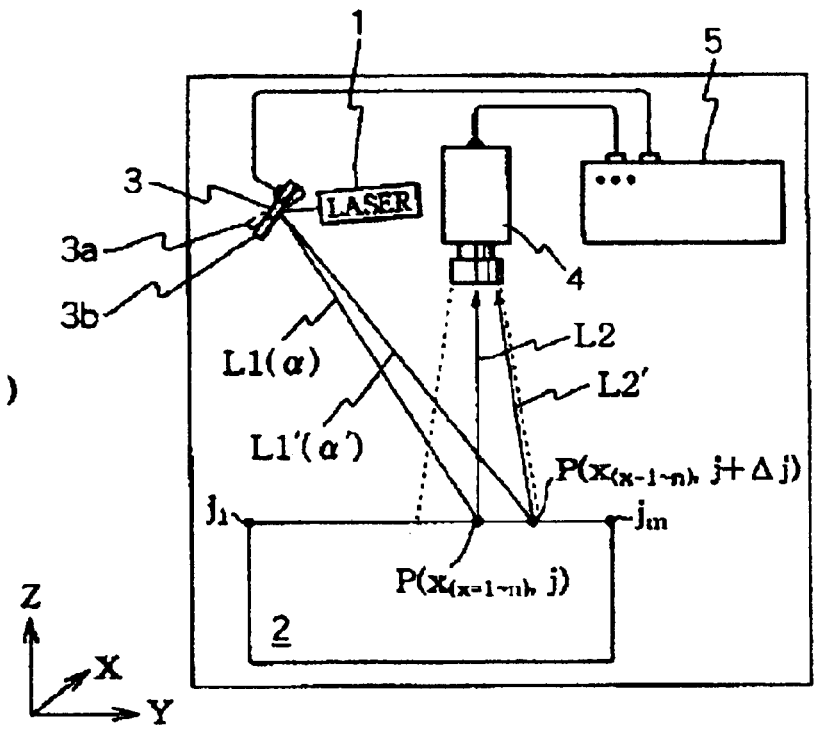

The light projector 1, the mirror 3, the camera 4 and the galvano scanner 8 as a mirror driving means have the same configurations and functions as those in the conventional example shown in FIG. 6(a). Thus, a detailed description thereof is omitted.

The image processing unit 10 also has the same configuration as that of the image processing unit 5 of the conventional example shown in FIG. 6(a), except for an internal processor and memory.

Figure 2:
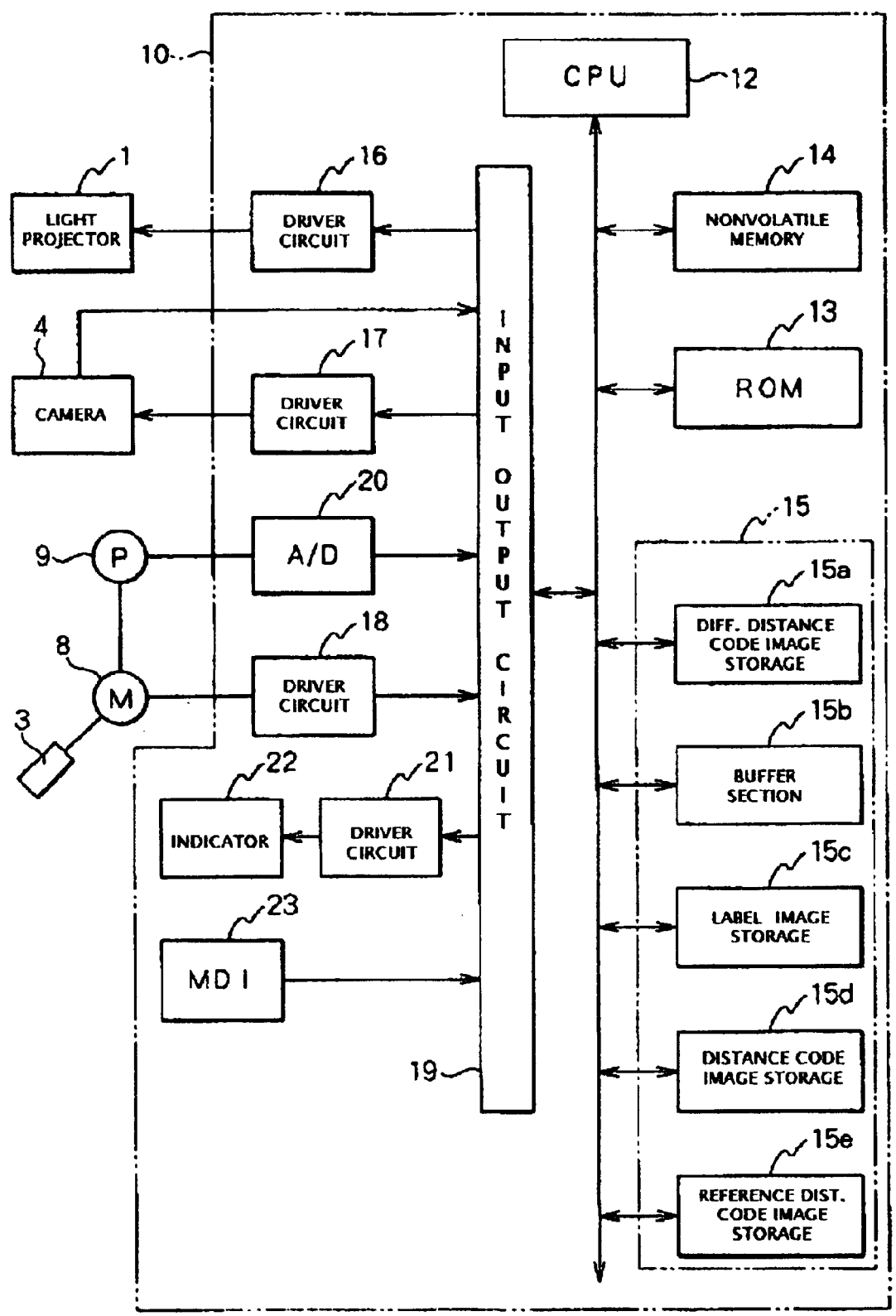
FIG. 2 is a functional block diagram, showing a schematic configuration of an image processing it in the defect inspection device.

FIG. 2 is a functional block diagram, showing a schematic configuration of the image processing unit 10. The figure also shows the electrical connections of the light projector 1, the galvano scanner 8, the rotating position detecting sensor 9, and the image processing unit 10.

As shown in FIG. 2, the image processing unit 10 has a CPU 12 for arithmetic processing, a ROM 13 containing a control program of the CPU 12, a nonvolatile memory to store a projection/recess shape of the perfect work 2, and a RAM 15 used for temporary storage or the like of arithmetic data. The storage region of the RAM 15 is used as a differential distance code image storage section 15a, a buffer section 15b, a label image storage section 15c, a distance code image storage section 15d, a reference distance code image storage section 15e. RAM 15 may also contain other functions (not shown or enumerated).

The light projector 1, the camera 4 and the galvano scanner 8 are each driven and controlled by the CPU 12 through driver circuits 16, 17 and 18 and an input-output circuit 19. The rotating position of the galvano scanner 8, which corresponds to the rocking position of the mirror 3, is detected by the rotating position detecting sensor 9. An A/D converter 20 produces a digital equivalent of the rotating position for connection through the input-output circuit 19 to the CPU 12.

The origin (or zero position) of the galvano scanner 8 sometimes shifts due to temperature differences. Even in the inspection precision of the rotating position detecting sensor 9 itself a nonlinear shift is sometimes found due to temperature changes. In strict sense, it is not possible to say tha the CPU 12 can accurately recognize the rocking position of the mirror 3.

As explained in the conventional art by referring to FIG. 6(a) and FIG. 6(b), an error is caused between actual levels of distance codes and levels of distance codes that the image processing unit 10 recognizes, due to a shift of rocking positions of the mirror due to temperature changes, or a detection error caused by temperature drift or the like of the rotating position detecting sensor 9 to detect the rocking positions of the mirror 3.

A display device 22 is connected to the input-output circuit 19 of the CPU 12 through a driver circuit 21. The display device 22 displays the final determination results of surface defects of the work 2 found by the arithmetic processing in the CPU 12.

A manual data input device 23 (MDI) constitutes a man-machine interface between the image processing unit 10 and an operator. The manual data input device 23 is used for starting the image processing unit 0, inputting measurement instructions and the like.

Figure 3:
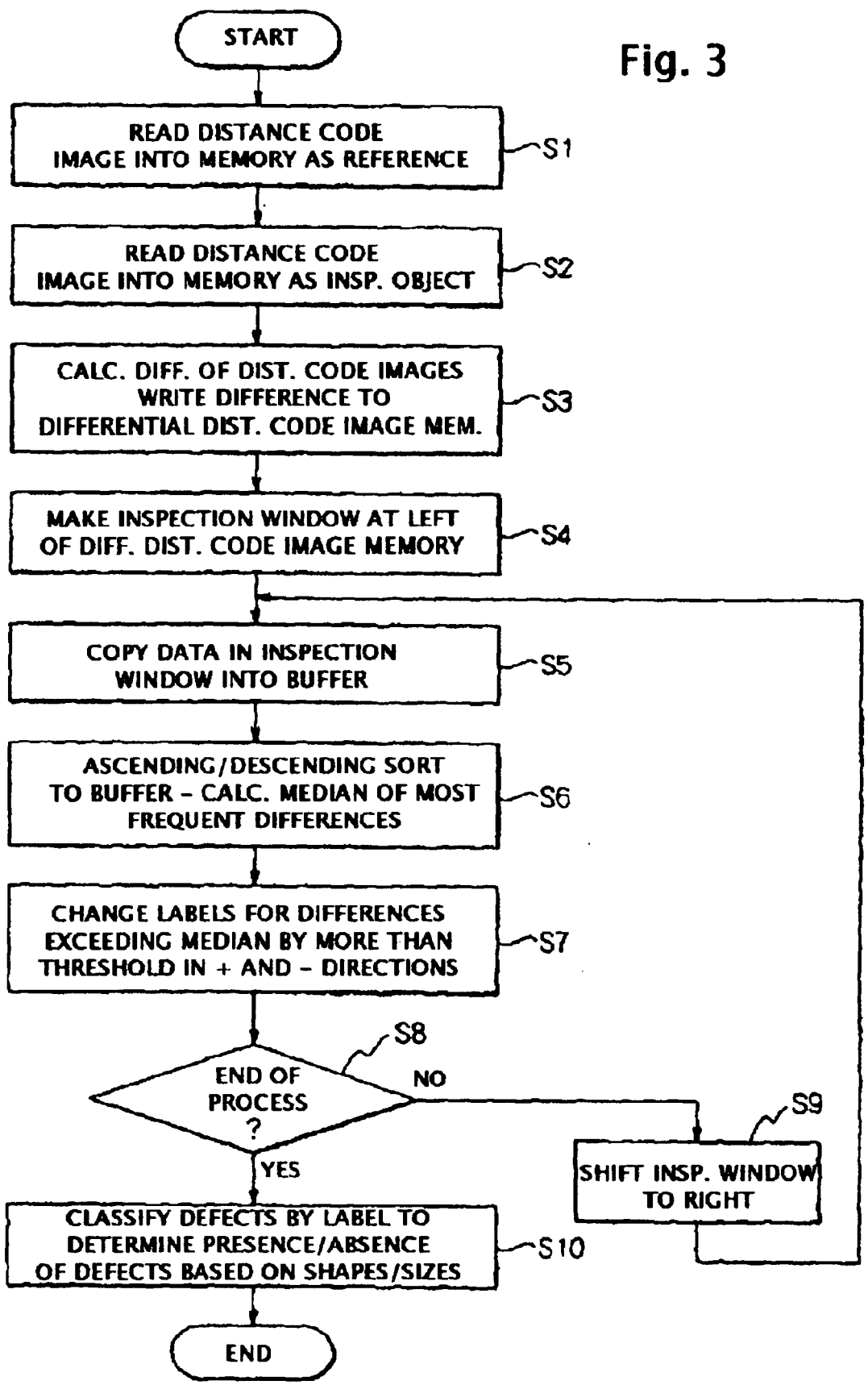
FIG. 3 is a flow chart showing schematic operations of the image processing unit in the defect inspection device.

The defect inspection method of a three-dimensional shape in the embodiment will be explained in detail by referring to the configurations and the flow chart in FIG. 3.

First, in preparation for determining defects on the surface of the inspected work 2, an operator stores a projection/recess shape of the perfect work 2 into the image processing unit 10 of the defect inspection device 7.

Specifically, an operator first places the perfect work 2 on a predetermined position of the work mounting table 11 in the defect inspection deice 7, and inputs measurement instructions for reference data input by operating the manual data input device 23.

Figure 7A:
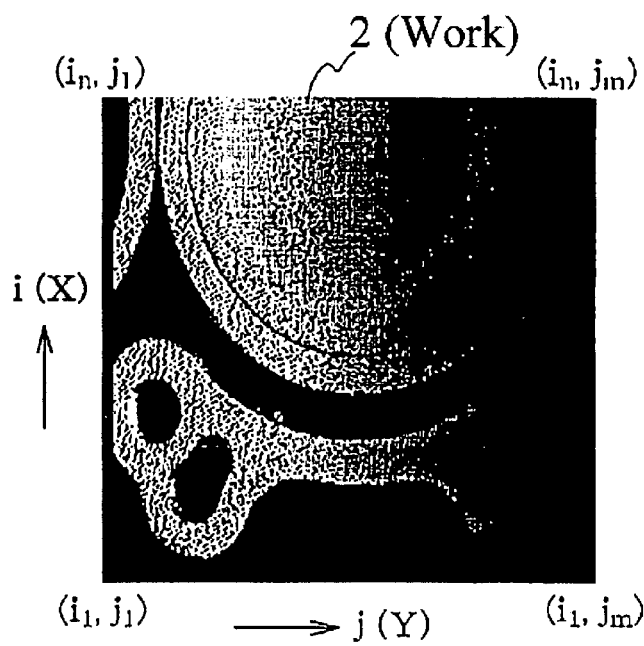
FIG. 7(a) is a conceptual diagram showing one example of a distance code image as a reference that is obtained by the conventional defect inspection method of a three-dimensional shape.
Figure 7B:
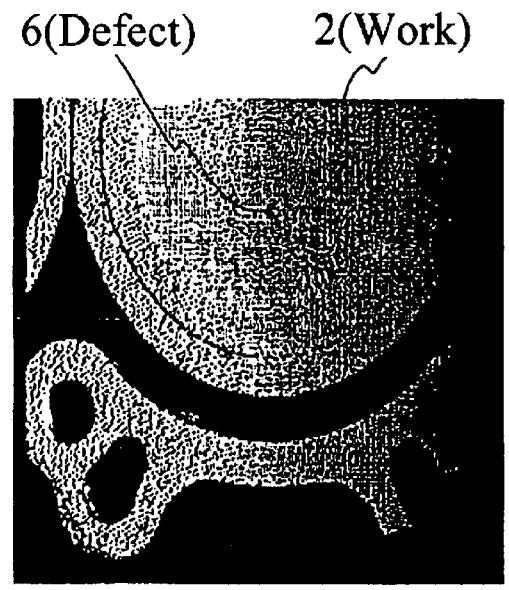
FIG. 7(b) is a conceptual diagram showing one example of a distance code image containing a defect that is obtained by the conventional defect inspection method of a three-dimensional shape.
Figure 7C:
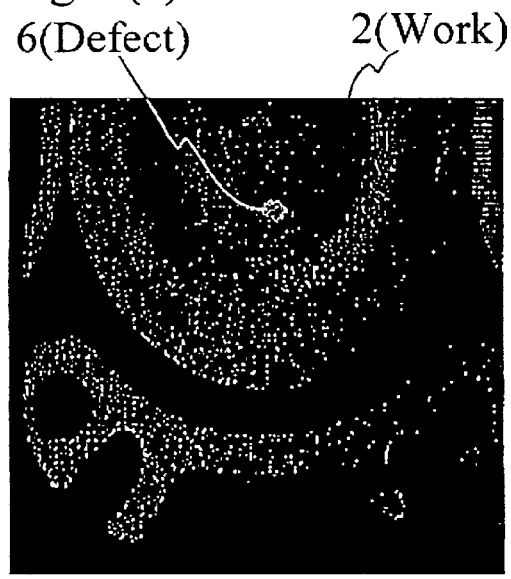
FIG. 7(c) is a conceptual diagram showing one example of a differential distance code image that is obtained by the conventional defect inspection method of a three-dimensional shape.
Figure 7D:
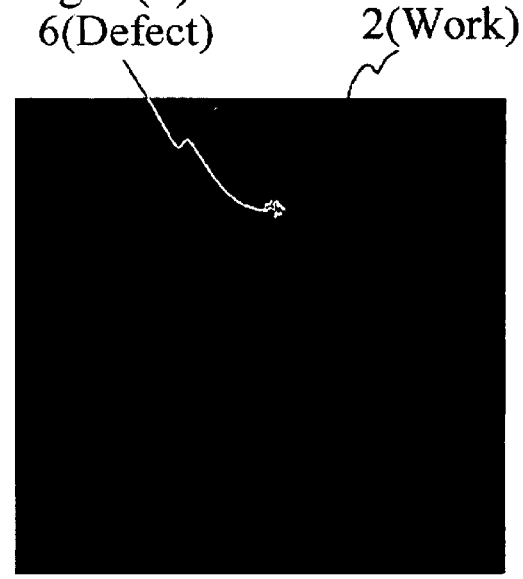
FIG. 7(d) is a conceptual diagram showing one example of a defect extracting image that is obtained by the conventional defect inspection method of a three-dimensional shape.

The image processing unit 10 detects the input of measurement instructions for reference data input and drives and controls the light projector 1, the camera 4 and the galvano scanner 8. As in the conventional art, the unit stores a projection/recess shape of the perfect work 2 into the nonvolatile memory 14 of the image processing unit 10 as a distance code image which becomes a reference, as shown in FIG. 7(a). The temperature (air temperature) that exists when a projection/recess shape of the perfect work 2, defined as the reference temperature, is stored by the reference data input processing. This reference temperature must be within a temperature range to properly operate the defect inspection device 7. However, as long as the reference is within the range, there is no particular limitation. For example, even when there is a slight shift from the origin of the mirror 3 or a slight temperature drift or the like of the rotating position detecting sensor 9, there is practically no hindrance.

In the embodiment, a value of X-axis coordinates at each position where the length of the irradiation 24 on the work 2 in a linear direction is divided by n is considered to be a matrix element $i_l$ to $i_n$ on a camera coordinate system. A value of Y-axis coordinates at each position in which an distance of rocking positions where the laser irradiates from the left end to the right end of the work 2 is divided by m is considered to be a matrix element $j_l$ to $j_m$ on a camera coordinate system in other words, there are n×m matrix elements $(i_l, j_l)$ to $(i_n$ to $j_m$ in the overall matrix.

The distance code value indicating the rocking angle of the mirror 3 is 255 (which corresponds to white in a gray scale) when the laser beam irradiates the left end of the work 2 at the reference temperature, and the value is 0 (which corresponds to black in a gray scale) when laser beam irradiates the right end of the work 2 at the reference temperature.

The image processing unit 10 stores rocking angles of the mirror 3 in response to the matrix of a laser beam detecting position on a camera coordinate system of the camera 3, in other words, distance codes. Thus, when there is a plane standing vertically on the work 2, that is, when the detection position of the laser beam within an X-Y plane does not change as the rocking angle of the mirror 3 changes, different distance codes are stored on the same matrix. In this case, a value which is finally stored in response to this matrix, is a distance code which is input at the end.

FIG. 7(*a*) is an image when a distance code value stored at each matrix element of $(i_{x\,(x=l\,to\,n)}, j_{y\,(y=l\,to\,m)})$ on a camera coordinate system is visualized as gray-scale density as the defect inspection device 7 is started at the reference temperature. This image is a distance code image as a reference.

However, the distance code image in FIG. 7(*a*) is simply visualized data for convenience of explanation. The distance code image is dealt with simply as numeric data for the internal processing of the image processing unit 10. Even a reference distance code image stored in the nonvolatile memory 14, in other words, data expressing a projection/recess shape of the perfect work 2, is numeric data of a three-dimensional array. It is not particularly necessary to display the distance code image of FIG. 7(*a*) on the display device 22.

The work 2 used for generating the distance code image as a reference is removed from the work mounting table 11 after operation.

Subsequently, in order to inspect defects on the surface of the inspected work 2, an operator similarly places the inspected work 2 on the work mounting table 11, and operates the manual data input device 23 to input measurement instructions for the defect inspection.

Figure 9A:
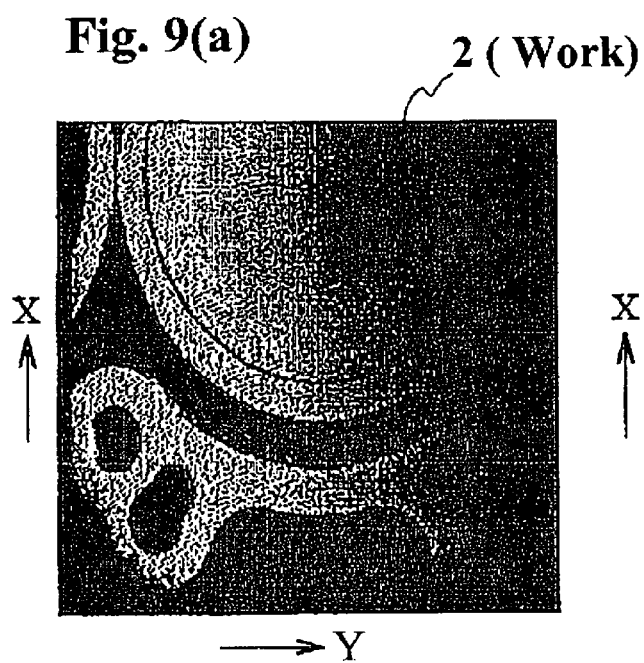
FIG. 9(a) is a conceptual view, showing one example of a distance code image generated on the basis of distance codes that are extracted by scanning a work at a temperature higher than a reference temperature.

After reading a reference distance code image obtained from the perfect work 2 from the nonvolatile memory 14 into the reference distance code image storage section 15*e* of the RAM 15 (step S1), the image processing unit 10 which detected the input of measurement instructions for defect inspection drives and controls the light projector 1, the camera 4, and the galvano scanner 8 for the above-mentioned reference data input processing. Then, the unit stores a projection/recess shape of the inspected work 2 into the distance code image storage section 15*d* of the RAM 15 as a distance code image, as shown in FIG. 9(*a*) (step S2).

The data array of a distance code image is exactly the same as the data array of the above-mentioned distance code image as a reference, so that the explanation thereof is omitted. However, differences are often found between distance codes stored as a distance code image and distance codes stored as a reference distance code image on the same matrix due to temperature changes or the like even if the shape of the inspected work 2 is perfect.

Subsequently, the image processing unit 10 finds the difference between a reference distance code image obtained from the perfect work 2 and a distance code image obtained from the inspected work 2 at each matrix element of $(i_{x\,(x=l\,to\,n)}, j_{y\,(y=l\,to\,m)})$. The unit then temporarily stores each difference value into the differential distance code image storage section 15*a* of the RAM 15 for each matrix element of $(i_{x(x=i\,to\,n)}, j_{y\,(y=l\,to\,m)})$ (step S3).

Figure 9B:
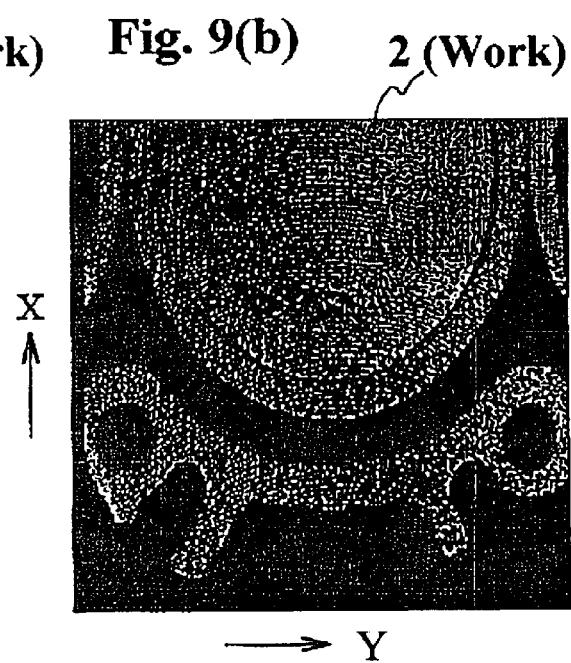
FIG. 9(b) is a conceptual view showing one example of a differential distance code image which is obtained by comparing a distance code image generated at the reference temperature and a distance code image generated at a temperature higher than the reference temperature.

If the scale of differences of distance codes is visualized as a gray-scale density as described above, a differential distance code image shown in FIG. 9(*b*), for instance, would be obtained. However, it is actually unnecessary to visualize a differential distance code image and display it on the display device 22.

Subsequently, the image processing unit 10 sets up an inspection window as shown in FIG. 4(*a*) at the differential distance code image storage section 15*a* (step S4). All the difference values contained in the inspection window are copied into the buffer section 15*b* of the RAM 15 (step S5). The content of the differential distance code image in FIG. 4(*a*) is the same as that of the differential distance code image in FIG. 9(*b*). The inspection window in FIG. 4(*a*) is conceptual like the distance code image and differential distance code image mentioned above, and is not actually displayed on the display device 22. In reality, each differential data for one vertical column which is equivalent to the matrix $(i_l, j_l)$ to $(i_n, j_l)$ on the camera coordinate system is extracted into the buffer section 15*b* by the processing of the above-mentioned step S4 and initially executing step S5.

Then, the image processing unit 10 performs an ascending or descending sorting process on all the differential data extracted to the buffer section 15*b*, to find a median of most frequent differential data (step S6).

Figure 5:
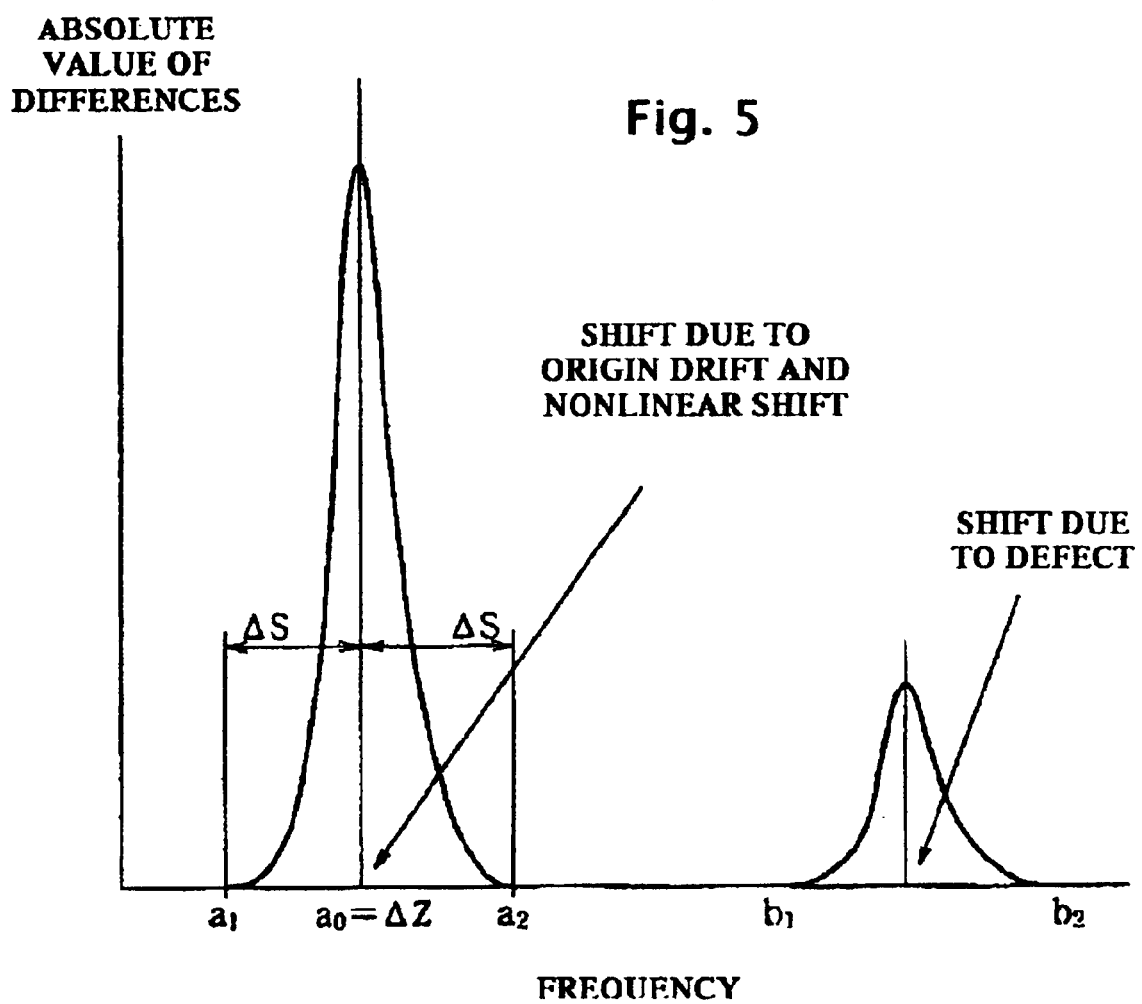
FIG. 5 is a conceptual diagram showing an example of sorting extracted differential data.

FIG. 5 shows one example of differential data which was sorted at step S6. In the example of FIG. 5, approximate differences are most frequently found between a1 and a2. Approximate differences are also frequently found between b1 and b2. In order to simplify arithmetic processing, a median $a_0$ of most frequent differences between a1 and a2 is defined as a most frequent difference value herein.

The median $a_0$, as described above, is (Z value, in other words, an error of distance codes caused by a position shift of the mirror 3 or a detection error (nonlinear shift, origin drift or the like) due to temperature drift or the like of the rotating position detecting sensor 9 for detecting the rocking position of the mirror 3. If a surface shape of the inspected work 2 is perfect, distance codes obtained from the inspected work 2 should perfectly match distance codes of a reference distance code image as all the distance codes are shifted for one vertical column by the most frequent difference value $a_0$ (=$\Delta Z$).

Then, the image processing unit 10 retrieves information on whether or not there are matrix elements having differences which deviate from the most frequent difference value $a_0$ by more than a threshold value (for instance, set value, $\Delta S$, in FIG. 5) in the buffer section 15*b*. If there are, the image processing unit 10 labels the matrix elements having those differences and stores them as defect candidates (step S7).

This labeling is, specifically, achieved by setting defect candidate flags at corresponding positions of defect candidates in the label image storage section 15c of the RAM 15 where the storage of n-row by m-column matrix elements is permitted, like the differential distance code image storage section 15a. For instance, if difference values at the (i4, j1) point and the (is, j1) point in a differential distance code image are contained at an distance between b1 and b2 in FIG. 5, defect candidate flags would be set at the (i4,j1) point and the (is,j1) point in the label image storage section 15c. The sections where the defect candidate flags are set are sections where distance codes obtained from the inspected work 2 does not match distance codes of a distance code image as a reference even by shifting the distance code data by the above-mentioned difference $a_0$ (=(Z). In other words, the sections indicate that the surface of the work 2 may have defects.

Figure 8:
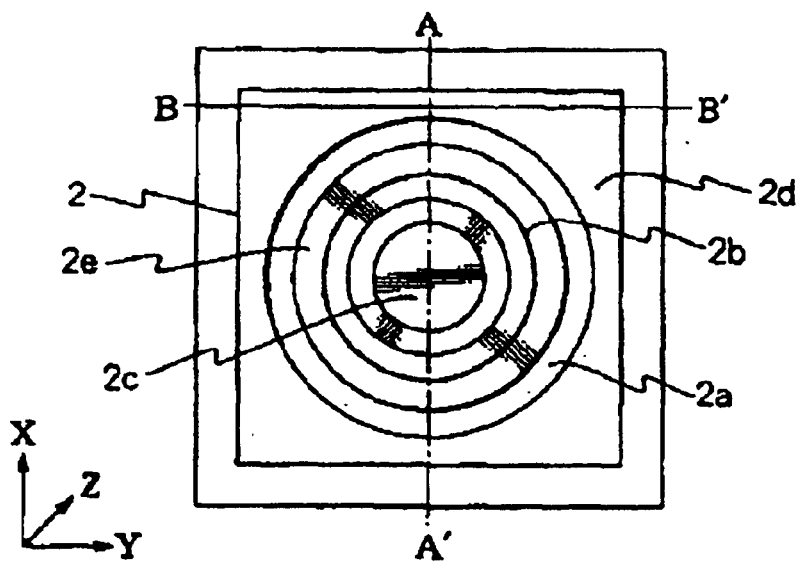
FIG. 8(a) is a plan view, showing one example of the shape of a work from which a distance code image is obtained.
FIG. 8(b) is a conceptual view, showing a work shape which is shown by extracted distance codes by scanning the work at a reference temperature, by adjusting the distance codes.
FIG. 8(c) is a conceptual view showing a work shape which is shown by extracted distance codes by scanning the work at a temperature higher than the reference temperature, by adjusting the distance codes.
FIG. 8(d) is a conceptual view, to which reference will be made in explaining conventional problems and some of the basic principles of the present invention.
FIG. 8(e) is a conceptual view to which reference will be made in explaining some of the basic principles of the present invention.
Figure 8:
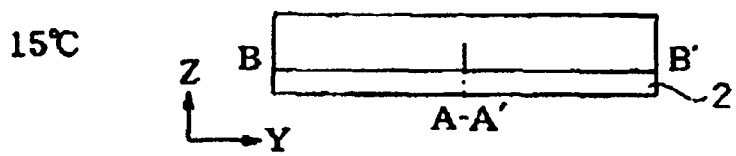
Figure 8:
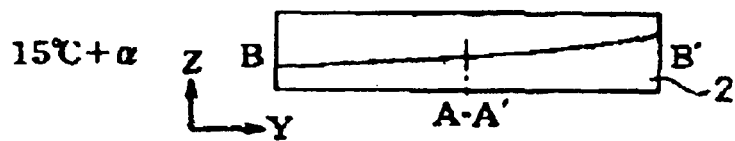
Figure 8:
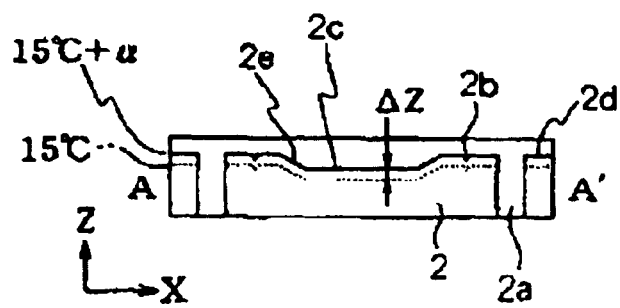
Figure 8:
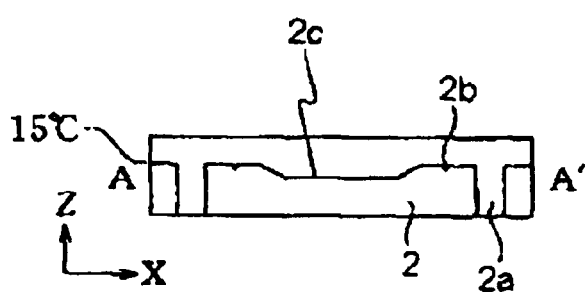

This labeling is essentially the same as the procedure in which a difference in both shapes is detected by overlapping a shape of the work 2 having no defects observed at the reference temperature with a shape of the inspected work 2 observed at a temperature higher or lower than the reference temperature, as shown in, for example, FIG. 8(e).

Subsequently, the image processing unit 10 determines whether or not the detection processing of defect candidates is finished for all the differences stored in the differential distance code image storage section 15a, in other words, whether or not the above-mentioned steps S5 to S7 are taken for all the columns j =1 to m (step S8). If the detection processing is not yet completed, the setting position of the inspection window is shifted in the column direction, in other words, the right direction in FIG. 4(a) (step S9). As described above, the steps S5 to S7 are repeatedly executed until all columns are scanned.

Finally, when the detection processing of defect candidates is completed for all the columns j =1 to m, the image processing unit 10 determines the presence/absence of defects of the inspected work 2 based on the existing state of all the labeled matrix elements. That is, the set/non-set state of defect candidate flags in the label image storage section 15c. Then, the unit displays the results on the display device 22 to notify an operator (step S10).

Figure 4A:
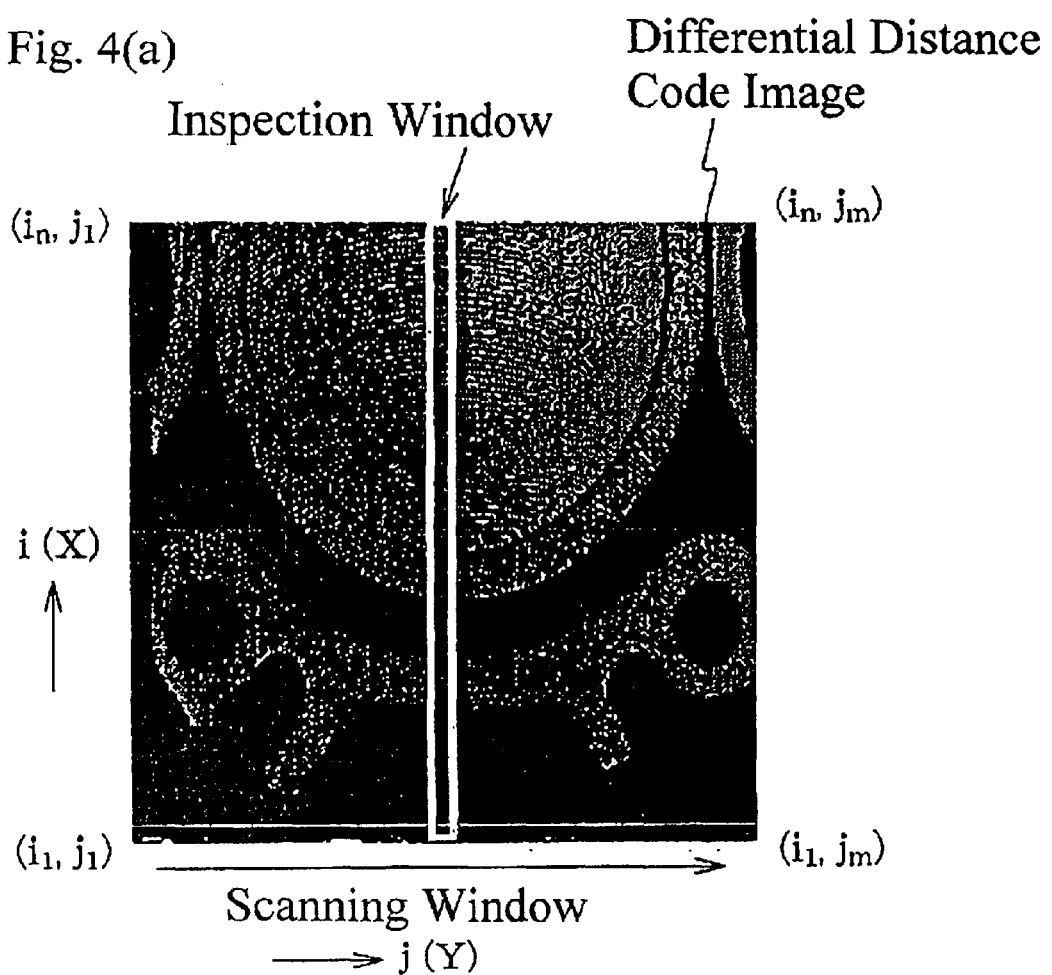
FIG. 4(a) is a conceptual diagram of an inspection window in order to specify differential data to be extracted from a differential distance code image.
Figure 4B:
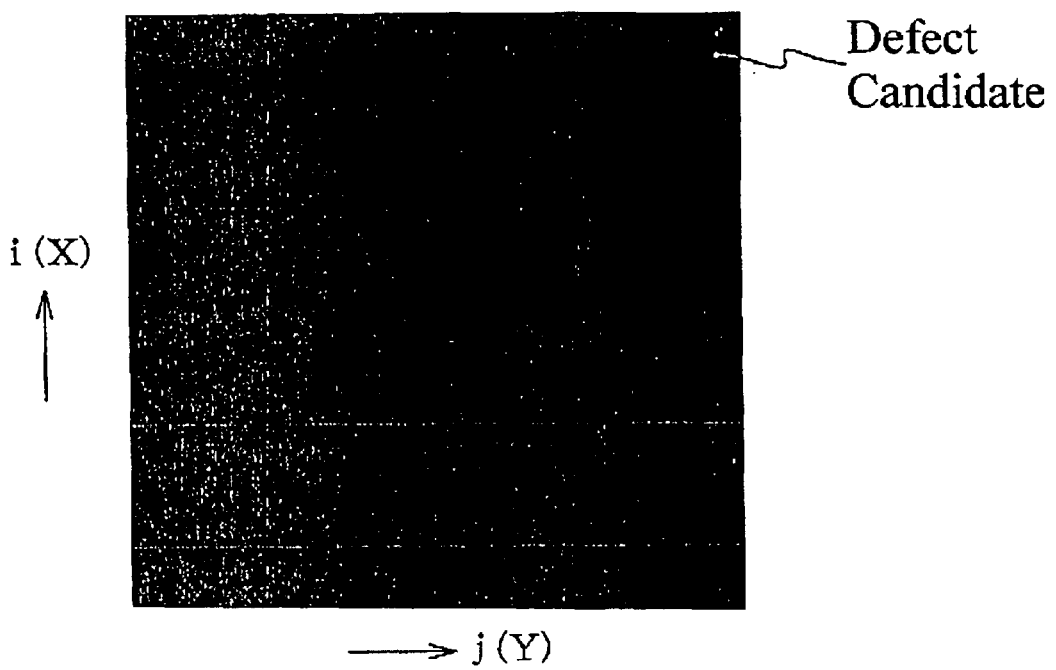
FIG. 4(b) is a conceptual diagram showing a visualized defect extracting image which is obtained by the image processing unit in the defect inspection device.

FIG. 4(b) shows one example of the ON/OFF state of defect candidate flags set on the label image storage section 15c by the repetition of the above-mentioned steps S5 to S7. The image is called a defect extracting image herein. This defect extracting image is also conceptual as described above. FIG. 4(b) visualizes the ON/OFF states of defect candidate flags by showing a section where a defect candidate flag is set in white, or a section where a defect candidate flag is not set in black. In the example of FIG. 4(b), white sections where defect candidate flags are set are scattered over a small area. As a result, the image processing unit 10 determines that the inspected work 2 has no defects, and displays a statement such as "no abnormality" on the display device 22.

When white sections where defect candidate flags are set are continuously found over an area larger than a certain level, a statement such as "defective" is displayed.

It is also possible to determine the presence/absence of defects by taking into account the whole shape of sections where defect candidate flags are set, in addition to the size of an area where defect candidate flags are set. For example, when the sections where defect candidate flags are set have a length greater than a certain value in each axis direction, this may he taken as an indication that the work 2 contains surface defects.

Figure 9C:
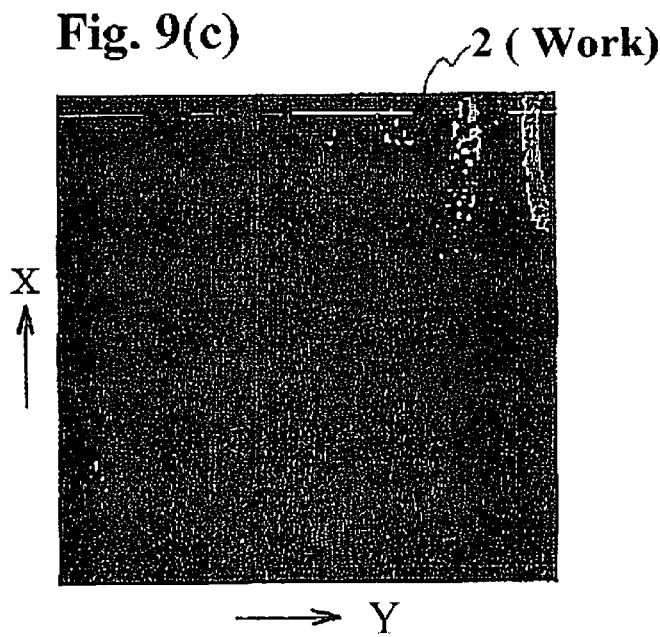
FIG. 9(c) is a conceptual view showing one example of a defect extracting image obtained from a differential distance code image by the conventional defect inspection method of a three-dimensional shape.

As clearly seen in a comparison between a defect extracting image in FIG. 4(b) obtained by the processing in the embodiment and a defect extracting image in FIG. 9(c) obtained by the conventional art, the embodiment prevents a determination mistake which results from an error of distance codes caused by a position shift of the mirror 3 or a detection error (nonlinear shift, origin drift or the like) due to temperature drift or the like of me rotating position detecting sensor 9 for detecting the rocking position of the mirror 3. The presence/absence of surface defects on the work 2 is properly determined.

The reason is, as described above, that a procedure is digitally executed for detecting a difference in both shapes by overlapping the shape of the work 2 having no defects observed at the reference temperature with the shape of the inspected work 2 observed at a temperature higher or lower than the reference temperature.

In the following, an embodiment is briefly explained. In the embodiment. most frequent distance codes are found among matrix elements in the linear direction of the radiation 24. That is, in the X-axis direction, at each rocking position of the mirror 3 for each projection/recess shape of the perfect work 2 and the projection/recess shape of the inspected work 2. Distance codes obtained for inspected work 2 are shifted at each rocking position of the mirror 3 so as to match the most frequent distance codes in the projection/recess shape of the perfect work 2 and projection/recess shape of the inspected work 2. Then, distance codes obtained from the perfect work 2 are compared with distance codes obtained from the inspected work 2 at each matrix element, so as to inspect the presence/absence of defects of the inspected work 2.

In this embodiment, first, the perfect work 2 is scanned by the defect inspection device 7 to produce a distance code image as a reference (as illustrated, for example in FIG. 7(a)). The distance code image is stored in the reference distance code image storage section 15e. The inspected work 2 is then scanned by the defect inspection device 7 to produce a distance code image as a reference (as illustrated, for example, in FIG. 9(a)). This image is stored in the distance code image storage section 15d.

Then, an inspection window as shown in FIG. 4(a) is set up by the image processing unit 10 at the reference distance code image storage section 15e. Distance codes of matrix elements equivalent to $(i_l, j_l)$ to , $(i_n,j_l)$ are extracted, and an ascending or descending sorting process is performed for all the extracted distance codes to find the most frequent distance codes. From the sorting results, the data shown in FIG. 5 are obtained. In this case, a group of most frequent distance codes is found only for the number of planes that are orthogonal to the optical axis of the camera 4. For instance, regarding an A–A' position shown in FIG. 8(a) for the work 2, a surface 2d, a flat part 2c, and the bottom section of the peripheral groove 2a become X, Y coordinates having frequent distance codes. Since the height of an inclined surface 2e is inconsistent, data from such an inclined surface does not become a frequent distance code. Moreover, a peripheral groove 2b is located in two dot shapes that are scattered at two locations. Thus the area thereof is extremely small, and the groove does not provide coordinates having frequent distance codes. Most frequent distance codes in the example of FIG. 8(a) and FIG. 8(d) are distance codes which are stored for coordinates of the flat part 2c (straight line having the maximum length in the linear direction of the irradiation on the work 2). A distance code equivalent to a reference surface of the normal work 2 as a reference (shape shown with a broken line in FIG. 8(d)) is specified based on the height of the flat part 2c.

The image processing unit 10 sets up an inspection window as shown in FIG. 4(a) at the distance code image storage section 15d . Then, distance codes of matrix elements equivalent to $(i_l, j_l)$ to $(i_n, j_l)$ are extracted. An ascending or descending sorting process is performed for all the extracted distance codes, as described above, to find the most frequent distance codes. As mentioned above, a distance code value equivalent to a reference surface of the inspected work 2 (shape shown with a solid line in FIG. 8(d)) is specified based on the height of the flat part 2c which consists of a straight line having the maximum length in the linear direction of irradiation on the work 2.

Subsequently, most frequent distance code values of the inspected work 2 are deducted from most frequent distance code values of the perfect work 2, thus finding a distance code difference ΔZ as shown in FIG. 8(d). This ΔZ, value is an error of distance codes, equivalent to a position shift of the mirror 3 or a detection error (nonlinear shift, origin drift, or the like) due to temperature drift or the like of the rotating position detecting sensor 9 for detecting, a rocking position of the mirror 3.

Then, the difference ΔZ is added to each distance code of $(i_l,j_l)$ to $(i_n, j_l)$ which was extracted from the distance code image storage section 15d. (In this embodiment, ΔZ has a minus sign.) Distance code values obtained from the inspected work 2 are all shifted, and are again written into the distance code image storage section 15d. Due to this procedure, a projection/recess shape of the perfect work 2 and a projection/recess shape of the inspected work 2 actually overlap each other at the flat part 2c as a reference as shown in, for instance, FIG. 8(e).

The above-mentioned procedure is repeatedly executed for all the data arrays $j_l$ to $j_m$ in the distance code image storage section 15d. Thus, an error ΔZ of a distance code that is characteristically found at each rocking position is found at each rocking position of the mirror 3. Distance code values obtained from the inspected work 2 are shifted only by the error ΔZ, and then re-loaded into the distance code image storage section 15d.

Finally, the presence/absence of defects on the surface of the inspected work 2 is determined by a comparison between distance codes obtained from the perfect work 2 and distance code values (whose data has already been shifted) obtained from the inspected work 2.

In this embodiment, a reference surface for alignment is a surface containing a straight line which has the maximum length in the linear direction of the irradiation on the work 2, in other words, a straight surface containing the coordinates which have most frequent distance-measuring codes in a plurality of matrix elements having an identical Y-axis value. Thus, a reference surface can often be the flat section 2c or the surface 2d, depending on the position of the irradiation. However, the reference surface equally and simultaneously changes at the reference distance code image storage section 15e and the distance code image storage section 15d, so that there is no problem for comparison.

Even in this embodiment, like the initially explained embodiment, a difference in both shapes is actually detected by overlapping a shape of the work 2 having no defects observed at the reference temperature, with a shape of the inspected work 2 observed at a temperature higher or lower than the reference temperature. Thus, it is possible to prevent an error of distance codes caused by a position shift of the mirror 3 or a detection error (nonlinear shift, origin drift or the like) due to temperature drift or the like of the rotating position detecting sensor 9 for detecting the rocking position of the mirror 3. The presence/absence of surface defects of the work 2 is appropriately determined.

In the defect inspection method of a three-dimensional shape according to the present invention differences are found between values indicating rocking angles of a mirror which are equivalent to distances between a perfect work and a camera, and values indicating rocking angles of the mirror which are equivalent to distances between an inspected work and the camera. The differences are stored in a matrix for which the linear direction of the irradiation and the direction of a moving locus of the irradiation are two orthogonal axes. The most frequent difference value among matrix elements in the linear direction of the irradiation is found at each rocking position. Matrix elements having differences that deviate from the most frequent difference by more than a set value are found. Accordingly, the method detects sections where the values indicating rocking angles of the mirror which are equivalent to distances between a perfect work and the camera and the values indicating rocking angles of the mirror which are equivalent to distances between an inspected work and the camera do not match each other even by relatively shifting the values indicating rocking angles of the mirror. The detected sections are stored as defect candidates. Furthermore, the method determines the presence/absence of defects of an inspected work based on all the existing states of matrix elements that could be defect candidates on a matrix. Thus, even when the precision of the rocking position of the mirror and the rotating position detecting means for detecting the rocking position of the mirror is reduced due to temperature changes, the method accurately determines the presence/absence of defects on the surface of an inspected work.

Moreover, the method determines the presence/absence of defects on the surface of an inspected work by finding values indicating most frequent rocking angles of the mirror among matrix elements in the linear direction of the irradiation at each column of matrix elements arranged in the direction of the irradiation for each projection/recess shape of a perfect work and each projection/recess shape of an inspected work. The values indicating rocking angles of the mirror obtained from the inspected work at each column of matrix elements arranged in the direction of the irradiation are shifted so as to match the values indicating the most frequent rocking angles of the mirror in the projection/recess shape of the perfect work and the projection/recess shape of the inspected work. Then, the method practically overlaps the projection/recess shape of the perfect work with the projection/recess shape of the infected work. Thus, even when the precision of the rocking position of the mirror and the rotating position detecting means for detecting the rocking position of the mirror is reduced due to temperature changes, the method accurately determines the presence/absence of defects on the surface of an inspected work.

As a result, defect inspection is accurately executed on the surface of a work without changing settings so as to accurately execute the defect inspection, and without actively controlling the temperature of the environment. Operations for defect inspection are simplified, and additional facilities to improve the inspection precision are unnecessary. Costs for plant and equipment investment are also reduced.

Having described preferred embodiments of the invention with reference to the accompanying drawings, it is to be understood that the invention is not limited to those precise embodiments, and that various changes and modifications may be effected therein by one skilled in the art without departing from the scope or Spirit of the invention as defined in the appended claims.

What is claimed is:

1. A defect inspection method for detecting surface errors in a three-dimensional shape, comprising:
repetitively scanning a light beam in a linear pattern on a first work;
said first work being a reference work having a desired surface shape;
storing reference images of said linear pattern on said first work, together with related information about positions of said light beam to produce a first matrix value at each position of said light beam;
repetitively scanning said light beani in said linear pattern on a second work;
said second work being an inspected work;
storing inspected images of said linear pattern on said second work, together with related information about positions of said light beam to produce a second matrix value at each position of said light beam;
finding a set of differences between each element of said first matrix and each corresponding element of said second matrix;
defining as defect candidates elements of said set of differences in which said difference exceeds a most frequent difference by a predetermined value; and
determining a presence of defects based on states of said defect candidates.

2. A defect inspection method according to claim 1 wherein the step of repetitively scanning includes:
rotating a scanning mirror about an axis;
reflecting a light beam from said scanning minor to illuminate a line on said work; and
moving said work in a direction orthogonal to said line.

3. A defect inspection method, for detecting surface errors in a three-dimensional shape, comprising:
repetitively scanning a light beam in a linear pattern on a first work;
said first work being a reference work having a desired surface shape;
storing reference images of said linear pattern on said first work, together with related information about positions of said light beam to produce a first matrix value at each position of said light beam;
repetitively scanning said light beam in said linear pattern on a second work, said second work being an inspected work;
wherein the step of repetitively scanning includes:
rotating a scanning mirror about an axis;
reflecting a light beam from said scanning minor to illuminate a line on said work; and
moving said work in a direction orthogonal to said line;
storing inspected images of said linear pattern on said second work, together with related information about positions of said light beam to produce a second matrix value at each position of said light beam;
wherein the step of storing related information about position includes storing instant angles of said scanning mirror;
finding a set of differences between each element of said first matrix and each corresponding element of said second matrix;
defining as defect candidates elements of said set of differences in which said difference exceeds a most frequent difference by a predetermined value; and
determining a presence of defects based on states of said defect candidates.

4. A surface-defect detection method :for a three-dimensional object comprising:
scanning a light beam over a surface of a perfect object;
storing first matrix of reflectances of said light beam from said perfect object;
scanning said light beam over a surface of an inspected object to produce a second matrix;
differencing reflectances of said light beam from said inspected object with corresponding elements in said matrix to form a difference matrix;
adding a most common value in said difference matrix to all elements in said second matrix to produce a corrected matrix;
differencing elements in said corrected matrix with corresponding elements in said first matrix;
defining elements in said corrected matrix which differ from corresponding elements in said first matrix by a predetermined amount as error candidates; and
examining patterns of said error candidates to detect errors in said surface of said inspected object.

5. A defect inspection method comprising:
finding and storing a first matrix of a projection/recess shape of a perfect work in advance;
finding a second matrix of a projection/recess shape of an inspected work;
finding a difference between a value of said first matrix with a corresponding element of said second matrix, and storing said differences as a difference matrix;
finding a most frequent value in said difference matrix; and
differencing elements in said difference matrix with said most frequent value to produce a candidate matrix; and
identifying elements in said candidate matrix exceeding a predetermined value as defect candidates.

6. A defect inspection method according to claim 5 further comprising examining a pattern of said defect candidates to identify defects.

* * * * *